United States Patent
King et al.

(10) Patent No.: US 9,035,099 B2
(45) Date of Patent: May 19, 2015

(54) PROCESS FOR MAKING ETHOXYLATED AMINE COMPOUNDS

(71) Applicant: Dow Global Technologies LLC, Midland, MI (US)

(72) Inventors: Stephen W. King, League City, TX (US); Daniel A. Aguilar, Lake Jackson, TX (US); Christophe R. Laroche, Lake Jackson, TX (US)

(73) Assignee: Dow Global Technologies LLC, United States of America (*) Notice: Subject to any disclaimer, the term of this patent is extended or adjusted under 35 U.S.C. 154(b) by 0 days.

(21) Appl. No.: 14/358,854

(22) PCT Filed: Nov. 28, 2012

(86) PCT No.: PCT/US2012/066733
§ 371 (c)(1),
(2) Date: May 16, 2014

(87) PCT Pub. No.: WO2013/095875
PCT Pub. Date: Jun. 27, 2013

(65) Prior Publication Data
US 2014/0330042 A1    Nov. 6, 2014

Related U.S. Application Data

(60) Provisional application No. 61/578,388, filed on Dec. 21, 2011.

(51) Int. Cl.
*C07C 213/04* (2006.01)

(52) U.S. Cl.
CPC ............................ *C07C 213/04* (2013.01)

(58) Field of Classification Search
None
See application file for complete search history.

(56) References Cited

U.S. PATENT DOCUMENTS 5,334,763 A * 8/1994 Washington et al. ......... 564/475
5,395,973 A * 3/1995 Washington et al. ......... 564/475

FOREIGN PATENT DOCUMENTS

| EP | 0004015 B1 * | 9/1979 | ............ C07C 89/02 |
| JP | 06247909 * | 9/1994 | ............ C07C 213/04 |

OTHER PUBLICATIONS

Japanese Patent Office machine translation of the Detailed Description of JP 06247909 A (Oct. 19, 2014).*
USPTO Scientific & Technical Information Center (STIC) provided machine translation of EP 0004015 B1 (Oct. 22, 2014).*
Database CAPLUS on STN, Acc. No. 2003:340165, Kwiatkowski et al., PL 174249 B1 (Jul. 31, 1998) (abstract).*

* cited by examiner

*Primary Examiner* — Brian J Davis

(57) ABSTRACT

An improved process for making ethoxylated amine compounds such as ethanolamines. The improvement comprises the addition of an acid to the amine compound prior to the addition of ethylene oxide to a reactor wherein the ethoxylated amine compound is prepared. The improvement reduces the concentration of undesirable glycol ether and/or vinyl ether ethoxylate byproducts which may contribute to undesirable properties, such as color and foaming, of the ethoxylated amine compounds.

9 Claims, No Drawings

PROCESS FOR MAKING ETHOXYLATED AMINE COMPOUNDS

CROSS REFERENCE TO RELATED APPLICATIONS

This application is a 35 USC §371 national phase filing of PCT/US2012/066733 filed Nov. 28, 2012, which claims the benefit of U.S. Application No. 61/578,388, filed Dec. 21, 2011.

BACKGROUND

This invention relates generally to an improved process for making ethoxylated amine compounds, such as ethanolamines. The improvement affords a higher purity product and reduces the concentration of undesirable glycol ether byproducts which may contribute to color formation, foaming, and other product quality issues associated with ethoxylated amine compounds.

Common byproducts in the manufacture of ethoxylated amine compounds include glycol ether amine byproducts, vinyl ether ethoxylates, and oligomers derived from condensations of acetaldehyde and amines. The undesirability of glycol ether amine byproducts is known, for example see U.S. Pat. Nos. 5,334,763 and 5,395,973 which disclose the reduction of ethoxylated or glycol ether amine byproducts in the production of mono-, di-, and triethanolamines by adding carbon dioxide. Use of carbon dioxide is undesirable for a number of reasons, including because it is a gas at ambient conditions and therefore more difficult to handle, and because the combination of amines and carbon dioxide can lead to corrosion issues. In addition, amine/carbonate salts, formed as byproducts, may not be thermally stable which may limit their use for reducing undesired glycol ether amine byproducts.

The above byproducts may contribute to unwanted color in ethoxylated amine formulations and/or the generation of foam during use, for example in such applications as hard surface cleaning, corrosion inhibition, and the like. Because such byproducts are also undesirable in certain commercial uses of ethoxylated amine compounds, it would be an improvement to have a process to make ethoxylated amine compounds having higher purity, better (e.g., less) color and a lower tendency to foam.

STATEMENT OF INVENTION

The invention is an improvement in a process and under conditions for making an ethoxylated amine compound from the reaction of ethylene oxide and an amine compound wherein undesirable byproducts are formed, the improvement comprises adding an acid to a reaction mixture comprising an amine compound selected from ammonia, a primary amine, a secondary amine, and mixtures of two or more thereof, prior to or concurrently with the addition of ethylene oxide to a reactor wherein the ethoxylated amine compound is prepared, provided that the ethoxylated amine compound is not piperazine or a piperazine derivative.

In some embodiments of the improved process, the acid is added to the reaction mixture prior to the addition of ethylene oxide to the reactor.

In some embodiments of the improved process of the invention the reaction mixture is anhydrous.

In some embodiments of the improved process the acid is present in an amount of from 0.001 to 5 weight percent based on the total weight of the reaction mixture.

In some embodiments of the improved process the acid is a mineral acid or an organic acid having a pKa of equal to or less than 13.

In some embodiments the acid is phosphoric acid, sulfuric acid, hydrochloric acid, boric acid, nitric acid, or a carboxylic acid such as acetic acid.

In some embodiments ethylene oxide is present in an amount of from 0.5 to 1.1 mol equivalents of ethylene oxide for each amine hydrogen (NH), based on the amount of amine compound.

In some embodiments the process is conducted at a reaction temperature of less than 250° C.

In some embodiments the acid is added to the reactor in a process for making ethanolamines.

In some embodiments the acid is added to the reactor in a process for making monoethanolamine.

In some embodiments the acid is added to the reactor in a process for making diethanolamine.

In some embodiments the acid is added to the reactor in a process for making triethanolamine.

In some embodiments, the acid is added to the reactor in a process for making diethanolamine (DEA) or triethanolamine (TEA) through the ethoxylation of recycled monoethanolamine (MEA) or diethanolamine respectively, or through the ethoxylation of mixtures of recycled monoethanolamine and diethanolamine.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

"Alkyl," as used in this specification encompasses straight and branched chain aliphatic groups. In some embodiments, alkyl contains 1 to 10, alternatively 1 to 8, or alternatively 1 to 6 carbon atoms. Preferred alkyl groups include, without limitation, methyl, ethyl, propyl, isopropyl, butyl, isobutyl, sec-butyl, tert-butyl, pentyl, and hexyl.

The term "cycloalkyl" refers to saturated and partially unsaturated cyclic hydrocarbon groups having 3 to 12 carbons, preferably 3 to 8 carbons, and more preferably 3 to 7 ring carbon atoms. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a C6-C12 aromatic moiety comprising one to three aromatic rings. Preferably, the aryl group is a C6-C10 aryl group. Preferred aryl include, without limitation, phenyl, naphthyl, anthracenyl, and fluorenyl. More preferred is phenyl.

A "heterocycloalkyl" group refers to a non-aromatic 3-12 atom ring system containing at least one nitrogen heteroatom and optionally one or more additional heteroatoms selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. Non-limiting examples of a heterocycloalkyl group include piperidine and morpholine.

The invention is based on the discovery that, in processes and under conditions for making ethoxylated amine compounds such as ethanolamines wherein undesired byproducts such as glycol ether amines, vinyl ether ethoxylates, and/or oligomers are formed, the levels of one or more of these undesirable byproducts, preferably the level of glycol ether byproducts or the level of vinyl ether ethoxylates or both, may be reduced or such byproducts substantially eliminated by the addition of even very small amounts (e.g., in some embodiments 1 weight percent or less) of an acid to a reactor wherein such ethoxylated amine compounds are prepared.

It is believed that the undesirable byproducts result from quaternary ammonium compounds and/or Hoffman-type degradation. For example, in the processes to make ethanolamines, common byproducts of these processes include the corresponding ethoxylated or glycol ether amines which are commonly referred to as MEAGE (monoethanolamine glycol ether), DEAGE (diethanolamine glycol ether), and TEAGE (triethanolamine glycol ether). These byproducts can be present in the refined ethanolamines and can impact the performance of the desired ethanolamines in end-use applications. Additionally, the formation of these byproducts can limit some process variables during the manufacture of ethanolamines. For example, the amount of MEA or DEA recycle to the reactor, or the direct ethoxylation of DEA can be limited due to byproduct formation. It is believed that these byproducts are the result of intermediate quaternary ammonium compounds such as 2-(tris(2-hydroxyethyl)ammonio) ethanolate (I) which are formed from the addition of ethylene oxide to TEA and of Hoffmann-type degradation of the intermediate quaternary ammonium compounds.

I

In addition to ethoxylated or glycol ether amine byproducts, other byproducts can be formed from the ethoxylation of MEA or DEA.

DEAGE

For example, a degradation of the quaternary ammonium intermediate can lead to acetaldehyde which condenses to give crotonaldehyde which can react with any free MEA in the process to give a Schiff base which can then undergo further reaction to give oligomers which can lead to colored products in the final product mixture.

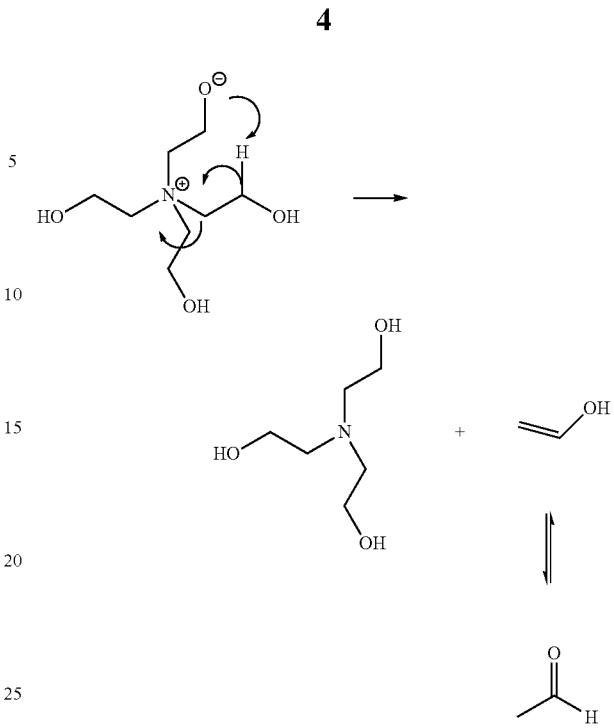

Additionally, if the quaternary ammonium intermediate has been ethoxylated the elimination can lead to vinyl ether ethoxylate oligomers such as 2-(2-(2-(vinyloxy)ethoxy) ethoxy)ethanol.

While not wishing to be bound by theory, it is believed that adding acid to the reaction mixture for the ethoxylation of amines results in reaction of the acid with the intermediate quaternary ammonium compounds thus inhibiting polyether formation and the Hoffman-type degradations which lead to byproducts which can impact product quality.

It will be evident to one skilled in the art, that the decomposition of the quaternary ammonium intermediate will depend on the structure, concentration, and temperature of the process. As a result, variables such as type of amine, feed rate of oxide, temperature and concentration of the reaction mixture may result in adjustments of the acid levels to mitigate the formation of byproducts.

In some embodiments of the invention, the amine compound may be represented by the formula:

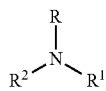

wherein R, R$^1$, and R$^2$ are each independently hydrogen, an alkyl group, a cycloalkyl group, an aryl group, —(CH$_2$—CH$_2$—O)$_n$—H wherein n is an integer from 1 to 8, a hydroxyalkyl group, an aminoalkyl group, or R, R$^1$ and the nitrogen to which they are attached form a heterocycloalkyl group, with the proviso that at least one of R, R$^1$ and R$^2$ is hydrogen.

In some embodiments, R, R$^1$, and R$^2$ are each independently hydrogen, an alkyl group or —(CH$_2$—CH$_2$—O)$_n$—H wherein n is an integer from 1 to 8, with the proviso that at least one of R, R$^1$ and R$^2$ is hydrogen.

In some embodiments, R, R$^1$, and R$^2$ are each independently hydrogen or —CH$_2$—CH$_2$—OH, with the proviso that at least one of R, R$^1$ and R$^2$ is hydrogen.

In some embodiments, the amine compound is piperidine or morpholine.

In some embodiments, the amine compound is ammonia.

In some embodiments, the amine compound is monoethanolamine.

In some embodiments, the amine compound is diethanolamine.

In the invention, the amine compound is not piperazine or a piperazine derivative. Thus, ethoxylated piperazines (including piperazine derivatives) are excluded from the invention.

An advantage of the present invention is that it permits the reaction of ethylene oxide and the amine compound to proceed with a significant reduction in the levels of the glycol ether amines and vinyl ether ethoxylate byproducts or their substantial elimination. In some embodiments, the amount of undesirable glycol ether amine byproducts is 0.5 area percent or less, preferably 0.1 area percent or less based on a stoichiometric equivalent of ethylene oxide for each NH functionality. The amount of undesirable glycol ether byproducts may be determined by gas chromatography or other methods known to one skilled in the art.

In the process of the invention, the ethoxylation of the amine compound may be accomplished under anhydrous and/or neat (without added solvent) conditions. If solvent is used, water is preferred. Preferably, the reaction is conducted without or with small amounts of added solvent, such as water, for instance 2 weight percent or less, alternatively 1 weight percent or less, based on the total weight of the reaction mixture.

Preferably, ethoxylation of the amine compound is accomplished by preparing a reaction mixture comprising the amine compound, from 0.001 to 5 weight percent of an acid based on the total weight of the reaction mixture, and from 0.5 to 1.1 mol equivalents, preferably 0.9 to 1 mole equivalents, of ethylene oxide per NH, based on the amount of the amine compound. Preferably the acid is added to the amine compound prior to the addition of ethylene oxide.

Preferably, the reaction temperature is equal to or less than 250° C., preferably equal to or less than 200° C., more preferably equal to or less than 170° C., more preferably equal to or less than 150° C. Preferably, the reaction temperature is equal to or greater than 40° C., preferably equal to or greater than 80° C., more preferably equal to or greater than 100° C., more preferably equal to or greater than 120° C. In some embodiments, the reaction temperature is between 80 and 150° C.

The ethoxylation reaction is allowed to proceed until the desired level of amine is converted to an ethoxylated amine compound, preferably equal to or greater than 50 percent conversion, more preferably equal to or greater than 60 percent conversion, more preferably equal to or greater than 70 percent conversion, more preferably equal to or greater than 80 percent conversion, more preferably equal to or greater than 90 percent conversion, and most preferably equal to or greater than 95 percent conversion of the amine compound to an ethoxylated amine compound.

If the reaction mixture is an aqueous solution, preferably the amine compound is present in an amount of equal to or less than 70 weight percent based on the total weight of the reaction mixture, preferably equal to or less than 60 weight percent, more preferably equal to or less than 50 weight percent based on the total weight of the reaction mixture. If the reaction mixture is an aqueous solution, preferably the amine compound is present in an amount of equal to or greater than 1 weight percent based on the total weight of the reaction mixture, preferably equal to or greater than 10 weight percent, more preferably equal to or greater than 20 weight percent based on the total weight of the reaction mixture.

We have found that the addition of a proton donor compound, referred to herein as an acid, such as an organic acid or mineral acid mitigates the formation of glycol ether byproducts during the preparation of ethoxylated amine compounds. Preferred acids are proton donor compounds having a pKa equal to or less than 13, more preferably a pKa equal to or less than 11, more preferably a pKa equal to or less than 9, and more preferably a pKa equal to or less than 5. Examples of suitable mineral acids are phosphoric acid, sulfuric acid, hydrochloric acid, boric acid, nitric acid, and the like. Examples of suitable organic acids are carboxylic acids such as but not limited to acetic acid.

Preferably the acid is added to the reaction mixture in an amount of equal to or less than 10 weight percent based on the total weight of the reaction mixture, preferably equal to or less than 5 weight percent, preferably equal to or less than 2.5 weight percent, more preferably equal to or less than 2 weight percent, even more preferably equal to or less than 1.5 weight percent, and even more preferably equal to or less than 1 weight percent based on the total weight of the reaction mixture. Preferably the acid is added to the reaction mixture in an amount of equal to or greater than 0.001 weight percent based on the total weight of the reaction mixture, preferably equal to or greater than 0.01 weight percent, and more preferably equal to or greater than 0.1 weight percent based on the total weight of the reaction mixture.

Preferably ethylene oxide is added to the reaction mixture in an amount of equal to or greater than 0.75 mol equivalents for each NH, preferably equal to or greater than 1 mol equivalents, preferably no greater than 1.1 mol equivalents for each NH based on the amount of amine compound.

A preferred application of the process of the invention is for the production of ethanolamines, particularly monoethanolamine, diethanolamine, or triethanolamine. Ethanolamines, such as monoethanolamine (MEA), diethanolamine (DEA) and triethanolamine (TEA), are produced commercially from ethylene oxide and ammonia under a variety of conditions. Adjustments to the MEA:DEA:TEA ratio to meet market demand can be made to favor one product over another. Relative amounts of the individual ethanolamines may be controlled by adjusting the ammonia-ethylene oxide feed ratio, by recycling MEA and/or DEA back to some point in the reactor, or by employing selective catalysts. For example, MEA may be preferentially produced through a large excess of ammonia in relation to ethylene oxide, and TEA may be preferentially formed by running at low ammonia to ethylene oxide mole ratios or recycle of MEA and or DEA back to some point in the reactor.

Another route to DEA and TEA includes reacting MEA and/or DEA with ethylene oxide in a separate reactor. The resulting mixtures are separated into individual components by distillation.

Some embodiments of the invention will now be described in the following Examples.

EXAMPLES

The ethoxylation reactions are performed in a jacketed, baffled 9 liter stainless steel autoclave reactor equipped with magnetically driven impeller.

Example 1 (Comparative)

Preparation of Triethanolamine from Diethanolamine and Ethylene Oxide (EO)

This example involves the ethoxylation of diethanolamine to prepare a sample with a nominal molar equivalent of EO/DEA of 0.75. Diethanolamine (1806 g) is charged into a previously nitrogen purged 9 L reactor. The reactor is pressurized then vented seven times to remove atmospheric oxygen, then pressurized with nitrogen to 110 to 140 kPa at ambient temperature. The reactor contents are heated with agitation at 120° C., then ethylene oxide (565 g total) is metered into the reactor over approximately 50 minutes at 120° C. resulting in an operating pressure of 340 to 415 kPa. After the EO feed is complete, the reactor contents are agitated at reaction temperature for an additional 2 hr to consume unreacted oxide (digest), then cooled to 30° C. The reaction mixture, analyzed by gas chromatographic analysis, indicates 0.14 area percent of 2-2-(2-hydroxyethoxy)-ethylaminoethanol (undesired byproduct) and 0.14 area percent of 2-(2-(2-(vinyloxy)-ethoxy)ethoxyethanol (undesired byproduct) has formed. The undesired byproducts are confirmed by electron impact mass spectrometry.

Example 2 (Inventive)

Preparation of Triethanolamine from Diethanolamine and Ethylene Oxide with Added Acetic Acid This example involves the ethoxylation of diethanolamine to prepare a sample with a nominal molar equivalent of EO/DEA of 0.75 in the presence of glacial acetic acid. A mixture of diethanolamine (1799 g) and glacial acetic acid (18.0 g) is charged into a previously nitrogen purged 9 L reactor. The reactor is pressurized then vented seven times to remove atmospheric oxygen, then pressurized with nitrogen to 110-140 kPa at ambient temperature. The reactor contents are heated with agitation at 120° C., then ethylene oxide (560 g total) is metered into the reactor over approximately 50 minutes at 120° C. resulting in an operating pressure of 340-415 kPa. After the EO feed is complete, the reactor contents are agitated at reaction temperature for an additional 3½ hr to consume unreacted oxide (digest), then cooled to 30° C. The reaction mixture, analyzed by gas chromatographic analysis, indicates 0.03 area percent of 2-2-(2-hydroxyethoxy)-ethylaminoethanol (undesired byproduct) and 0.07 area percent of 2-(2-(2-(vinyloxy)-ethoxy)ethoxyethanol (undesired byproduct) has formed. The undesired byproducts are confirmed by electron impact mass spectrometry.

Example 3 (Inventive)

Preparation of Triethanolamine from Diethanolamine and Ethylene Oxide with Added Sulfuric Acid/Water The reaction conditions as described in Example 2 are used to prepare a sample with a nominal molar equivalent of EO/DEA of 0.75 except sulfuric acid/water (1.1 wt %/9.8 wt % of total reaction mixture) is added to diethanolamine instead of acetic acid. The reaction mixture, analyzed by gas chromatographic analysis, indicates no detectable amounts of 2-2-(2-hydroxyethoxy)-ethylaminoethanol (undesired byproduct) or 2-(2-(2-(vinyloxy)-ethoxy)ethoxyethanol (undesired byproduct) are formed.

The GC analyses show that under essentially the same reaction conditions the addition of 1% acetic acid to diethanolamine (DEA) results in less glycol ether of DEA (2-2-(2-hydroxyethoxy)ethylaminoethanol) and 2-2-(2-hydroxy-ethoxy)-ethylaminoethanol being formed when 0.75 equivalents of ethylene oxide are added. When 12.5% water and 1.4% sulfuric acid is added to diethanolamine no detectable amounts of (2-2-(2-hydroxyethoxy)ethylaminoethanol) and 2-2-(2-hydroxy-ethoxy)-ethylaminoethanol were formed.

The potential amine glycol ether impurities for DEA ethoxylation include the following:

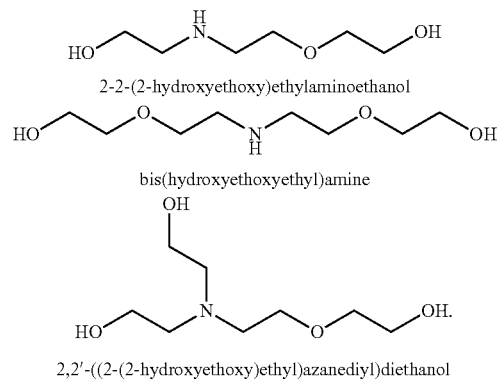

In addition vinyl ether ethoxylates such as 2-(2-(2-(vinyloxy) ethoxy)ethoxy)ethanol can be formed when ethoxylating DEA.

What is claimed is:

1. In a process and under conditions for making an ethoxylated amine compound from the reaction of ethylene oxide and an amine compound wherein undesirable amine glycol ether byproducts and/or vinyl ether ethoxylates are formed, the improvement comprises adding an acid to a reaction mixture comprising an amine compound selected from ammonia, a primary amine, and a secondary amine, prior to or concurrently with the addition of ethylene oxide to a reactor wherein the ethoxylated amine compound is prepared, provided that the ethoxylated amine compound is not piperazine or a piperazine derivative, with the proviso that the acid is present in an amount of from 0.001 to 10 weight percent based on the total weight of the reaction mixture, and with the proviso that ethylene oxide is present in an amount of from 0.5 to 1.1 mol equivalents of ethylene oxide for each NH moiety based on the amount of amine compound.

2. The improved process of claim 1 wherein the acid is a mineral acid or an organic acid having a pKa of equal to or less than 13.

3. The improved process of claim 1 wherein the acid is phosphoric acid, sulfuric acid, hydrochloric acid, boric acid, nitric acid, or a carboxylic acid.

4. The improved process of claim 1 wherein ethylene oxide is present in an amount of from 0.9 to 1.0 mol equivalents of ethylene oxide for each NH based on the amount of amine compound.

5. The improved process of claim 1 wherein the process is conducted at a reaction temperature of 250° C. or less.

6. The improved process of claim 1 wherein an acid is added to the reactor in a process for making monoethanolamine, diethanolamine, or triethanolamine.

7. The improved process of claim 1 wherein an acid is added to the reactor in a process for making diethanolamine or triethanolamine through the ethoxylation of recycled monoethanolamine or diethanolamine respectively, or through the ethoxylation of mixtures of recycled monoethanolamine and diethanolamine.

8. The improved process of claim 1 wherein ethylene oxide is present in an amount of from 0.75 to 1.0 molar equivalents of ethylene oxide for each —NH moiety.

9. The improved process of claim 1 wherein the acid is present in an amount of from 0.001 to 5 weight percent based on the total weight of the reaction mixture.

\* \* \* \* \*